(12) United States Patent
Brown

(10) Patent No.: US 9,283,117 B2
(45) Date of Patent: Mar. 15, 2016

(54) EYE MARKER DEVICE

(75) Inventor: Alan Wesley Brown, Wrightsville Beach, NC (US)

(73) Assignee: MINDSKID LABS, LLC, Wilmington, NC (US)

(*) Notice: Subject to any disclaimer, the term of this patent is extended or adjusted under 35 U.S.C. 154(b) by 208 days.

(21) Appl. No.: 13/427,253

(22) Filed: Mar. 22, 2012

(65) Prior Publication Data

US 2012/0245609 A1    Sep. 27, 2012

Related U.S. Application Data

(60) Provisional application No. 61/466,506, filed on Mar. 23, 2011.

(51) Int. Cl.
*A61B 17/00*    (2006.01)
*A61F 9/013*    (2006.01)

(52) U.S. Cl.
CPC .................................. *A61F 9/0136* (2013.01)

(58) Field of Classification Search
CPC .... A01K 11/005; A01K 11/00; A61F 9/0136; A61F 9/007
USPC .............. 606/166, 1, 116, 117; 351/212
See application file for complete search history.

(56) References Cited

U.S. PATENT DOCUMENTS

| | | | | |
|---|---|---|---|---|
| 4,875,767 A | * | 10/1989 | Wright | 351/212 |
| 5,084,059 A | * | 1/1992 | Metzger | 606/166 |
| 5,220,361 A | | 6/1993 | Lehmer et al. | |
| 5,455,645 A | * | 10/1995 | Berger et al. | 351/223 |
| 5,557,352 A | * | 9/1996 | Nordquist | 351/237 |
| 5,964,747 A | * | 10/1999 | Eaton et al. | 606/4 |
| 2004/0167540 A1 | * | 8/2004 | Gerten | 606/116 |
| 2007/0048064 A1 | * | 3/2007 | Tong et al. | 401/107 |

FOREIGN PATENT DOCUMENTS

DE    202010012367    11/2010

* cited by examiner

*Primary Examiner* — Tuan V Nguyen
*Assistant Examiner* — Tin Nguyen
(74) *Attorney, Agent, or Firm* — Williams Mullen, PC; Richard T. Matthews

(57) ABSTRACT

The present invention provides methods and systems for an eye marker device that includes a handle having an interior cavity, a marking means coupled to the handle, and a rotational scale for providing a visual representation of the angle of the marking means relative to a predetermined origination point.

10 Claims, 12 Drawing Sheets

EYE MARKER DEVICE

CROSS REFERENCE TO RELATED PATENT APPLICATION

The current application claims the benefit of the earlier priority filing date of the provisional application, Ser. No. 61/466,506, that was filed on Mar. 23, 2011.

FIELD OF THE INVENTION

The present invention relates generally to an eye marker device and more generally relates to an eye marker device that is internally weighted for providing a mark or indicator on the surface of the eye.

BACKGROUND OF THE INVENTION

The current invention addresses the problem of long lasting accurate ink marks applied to the ocular surface as needed for the correction of astigmatism.

In the field of refractive surgery there exists a need to place ink marks on the eye in order to orient the treatment of astigmatism. Astigmatism is a condition where the shape of the cornea bends light to more than one focal point causing a blurred image upon the retina. Astigmatism caused by the cornea is described as corneal astigmatism or corneal cylinder. It can be treated by altering the shape of the cornea through incisions or laser means so the light entering the eye is refracted to one focal point. Alternatively, in the field of cataract surgery, the corneal astigmatism can be balanced by an intraocular toric lens implant that has a curved surface that counterbalances the corneal astigmatism. Regardless of the means of treatment of astigmatism, the eye has to be marked before surgery in order to properly position the treatment of the astigmatism.

The current means of marking the eye generally involves the use of metal corneal markers. In most cases, the metal marker has projections that will touch the cornea or sclera. Ink from a sterile surgical marker is transferred from the ink marker to the projections of a sterilized metal marker. This thin layer of ink is then transferred to the eye by compressing the metal marker projections against the anesthetized cornea. All markers currently used suffer from issues of inadequate ink transfer to the eye surface principally due to the fact that only a thin layer of ink is being transferred to an ocular surface and that surface is wet from the ocular tear film. The ink marks so placed are blinked off within minutes. Because the marks are so short lived they must be placed immediately before the surgery begins.

All patients are now required to have the operative site marked with a surgical marker before being brought into the operating room. A review of the general steps used to mark a patient's eye before surgery will help better understand the full extent of the challenges facing the surgeon and patient.

Sequence Option 1: Marking in the Operating Room
1. After the patient has been sedated and has been marked over the operative eye brow they are brought into the operating room on a stretcher in a generally reclined position.
2. The patient is then asked to sit up in a vertical position for the surgeon to mark the eye with a sterile metal marker that has been inked with a sterile surgical ink marker and that has had its directional marking fins rotated to the desired astigmatic axis.
3. The patient then lies down and is prepped and draped for surgery with marks in the proper position for surgery.

It is well known that the position of the eye rotates or undergoes cyclotorsion when the patient moves from a vertical or sitting position to a lying or horizontal position. The error in marking an eye with the patient lying down can be in the 20 degree range which is very clinically significant. Consequently, the eye must be marked with the patient in the sitting or vertical position since this is the normal position of use for the eyes. This requirement conflicts with the typical operating room sequence of having the patient lying down, prepped, draped and ready for the surgeon before the surgeon enters the operating room. The need for the patient to be marked in the sitting position by the surgeon delays the normal prep sequence for surgery. An alternative sequence is to have the patient pre-marked in another patient preparation area where oral sedation and IVs are administered. The pre marking is done with a surgical ink marker pen applied to the area where the cornea meets the sclera. These markers leave a lasting dot of ink not found with the thin film of ink applied with sterile metal markers. The sequence in these cases is as follows:

Sequence Option 2: Marking in Preoperative Area
1. Patient is asked to sit up straight and fixate on a distant object. The surgical marker is applied to the eye in the horizontal and, when possible, vertical meridians.
2. Once the remainder of the patient preparation is accomplished the patient is moved to the operating room where they are prepped and draped for surgery, and are placed recumbent since the eye has preplaced ink dots that identify the position of the eye when the patient is upright.
3. The surgeon begins by identifying the previously placed surgical marker marks.
4. A sterile metal marker that has been inked with a new sterile marking pen is then used with the previously placed reference marks to properly place the astigmatic axis marks of the sterilized metal marker.

This sequence is more efficient because surgeons are required now to mark the patient's brow over the eye having surgery prior to being moved to the operating room. Because every patient gets marked with a surgical marker over the brow, it is convenient for the surgeon to add marks on the eye at the same time. Because metal markers retain only a thin film of ink that is blinked off within a few minutes, they cannot be used for marking outside of the operating room. Consequently, the only lasting marks that can be made before surgery are ink dots placed in the general horizontal and vertical meridians.

Clearly the above system to mark the eye for the treatment of astigmatism is complex and creates limitations as to the accuracy of the marks placed, how the procedure is performed and how the patient flow is achieved. In order to alleviate the above disadvantages the current invention is presented herein.

BRIEF SUMMARY OF THE INVENTION

According to an embodiment of the present invention, an eye marker device that includes a handle having an interior cavity, a marking means coupled to the handle, and a rotational scale for providing a visual representation of the angle of the marking means relative to a predetermined origination point.

According to another embodiment of the present invention, an eye marker device that includes a marking head with a marking end and a posterior end that contains at least one marking tip disposed on the marking end.

According to yet another embodiment of the present invention, an eye marker device that includes a marking head with at least two marking tips.

According to yet another embodiment of the present invention, an eye marker device that includes at least one weight disposed within the handle for providing balance and stability and/or rotational alignment to the eye marker device.

According to yet another embodiment of the present invention, an eye marker device that includes a bearing positioned within the interior cavity of the handle having a centrally located bore for receiving a hollow mounting shaft, wherein at least one weight is rotationally engaged to the hollow mounting shaft for providing balance and stability and/or rotational alignment to the eye marker device.

According to yet another embodiment of the present invention, an eye marker device that includes a handle having an interior cavity, a marking means coupled to the handle, a light source allowing light to shine through the interior cavity of the handle, and a rotational scale for providing a visual representation of the angle of the marking means relative to a predetermined origination point.

According to yet another embodiment of the present invention, an eye marker device that includes a marking means that is disposable.

According to yet another embodiment of the present invention, an eye marker device that includes a post having a first end and a second end, a marking head engaged to the first end of the post and having a marking end and a posterior end, whereby the first end of the post is engaged to the posterior end of the marking head. The eye marker device further includes at least one marking tip engaged to the marking end of the marking head, and at least one support means disposed on the post for providing stability and support to the post.

According to yet another embodiment of the present invention, an eye marker device that includes a light source that is an LED disposed on an enclosed electrical circuit.

According to yet another embodiment of the present invention, an eye marker device that includes a sleeve for enclosing the marking means.

According to yet another embodiment of the present invention, a marking means that includes a post having a first end and a second end, and a marking head engaged to the first end of the post. The marking head having a marking end and a posterior end, whereby the post is engaged to the posterior end and at least one marking tip disposed on the marking end of the marking head.

According to yet another embodiment of the present invention, a marking means that includes a fixation device positioned on the marking head.

According to yet another embodiment of the present invention, a marking means that includes a second end of the post designed to be coupled with a handle.

According to yet another embodiment of the present invention, a marking means that includes at least one support means extending axially along the post for providing stability and support.

According to yet another embodiment of the present invention, a marking means that includes an annular ring surrounding the post and containing a position indicator on the exterior surface of the annular ring.

According to yet another embodiment of the present invention, a marking means that includes a marking tip that is pre-inked.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

Figure 1A:
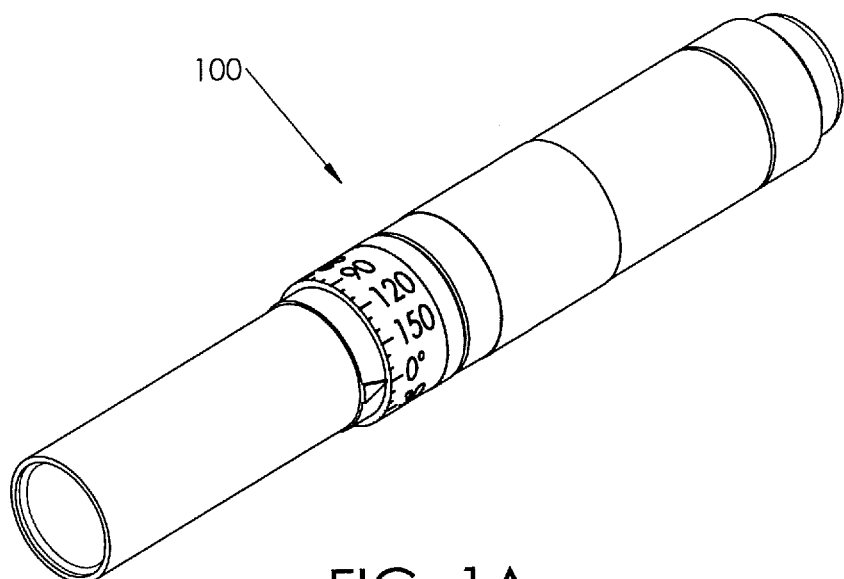
FIG. 1A is a perspective view of the eye marker device with an illuminating weighted handle.
Figure 1B:
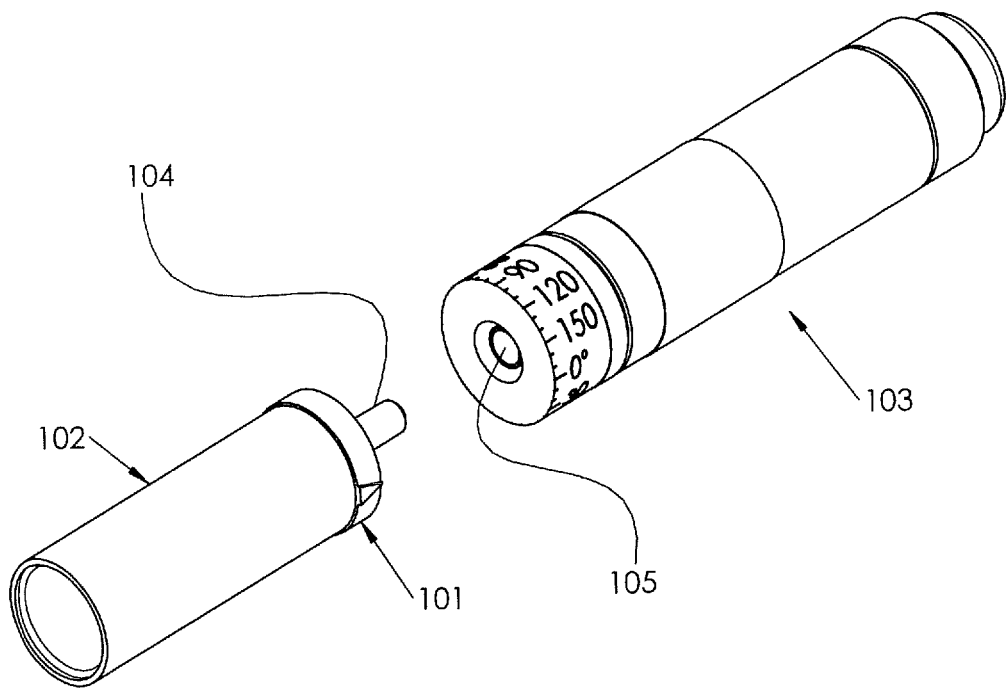
FIG. 1B is an exploded view of the eye marker device with an illuminating handle of FIG. 1A.
Figure 2:
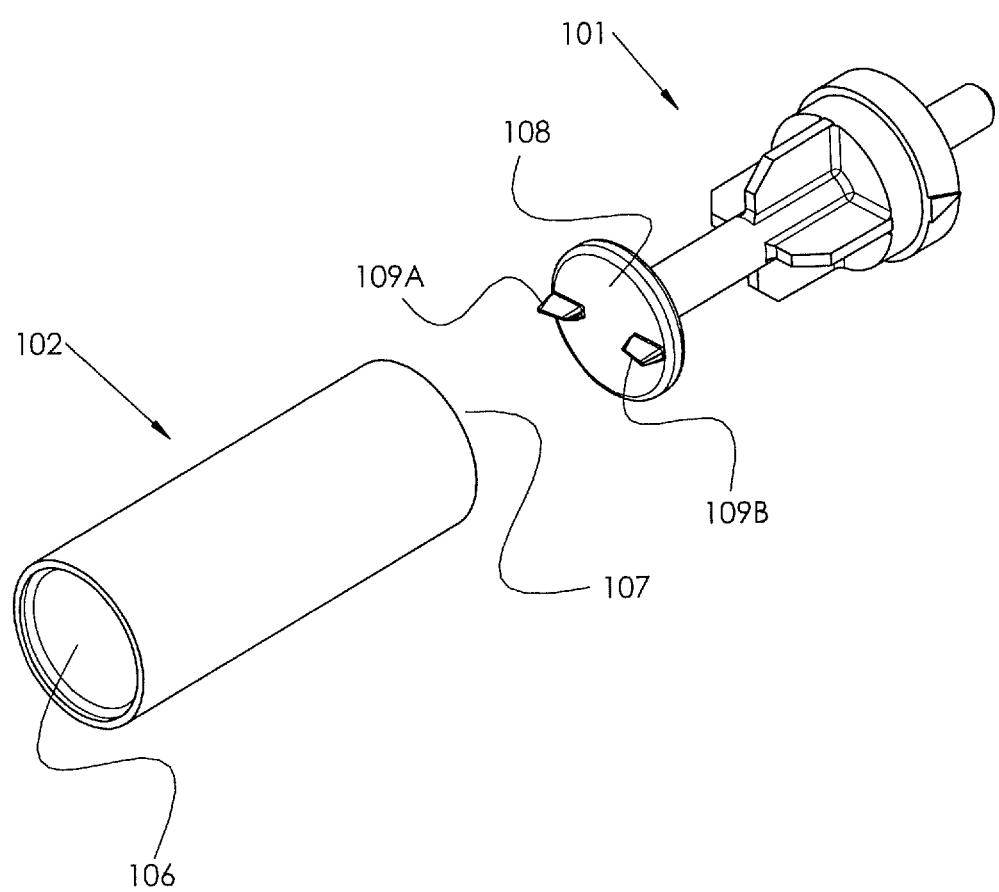
FIG. 2 is an exploded view of the tip and sleeve of the embodiment of FIG. 1A.
Figure 3:
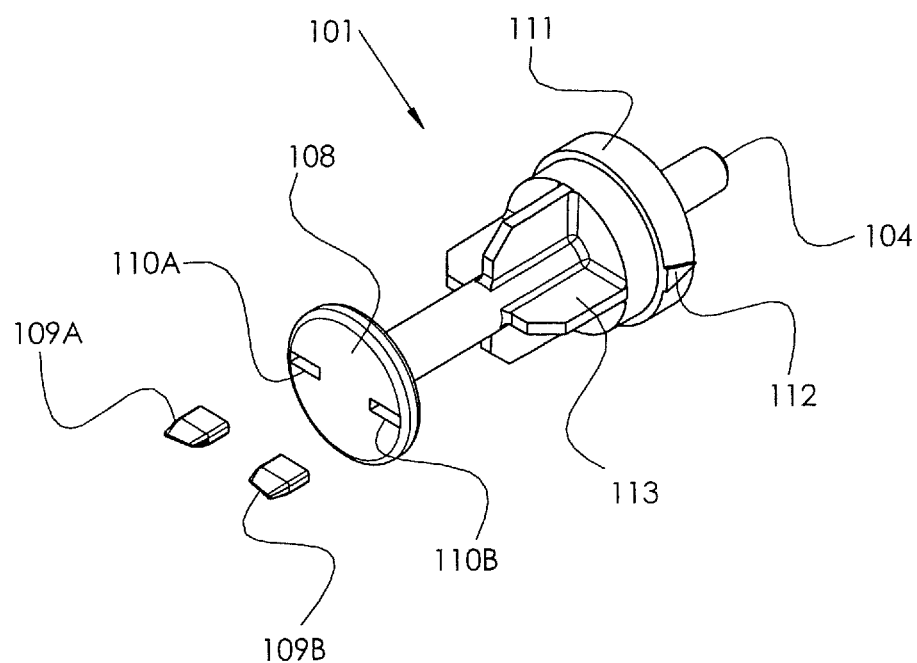
FIG. 3 is an exploded view of the tip.

Referring now specifically to the drawings, an eye marker device is illustrated in FIGS. 1A and 1B and is shown generally at reference numeral 100. The device 100 comprises a marking means 101, and a sleeve 102 that is assembled to a handle 103. One embodiment of the marking means 101, as shown in FIGS. 2 and 3, contains a post 104 with a first end and a second end. A marking head 108 is disposed on the first end of the marking means 101 and contains a marking end and a posterior end. The marking head 108 is generally cylindrical in shape, but may be alternatively shaped, by way of example only, and not limited to, generally square, generally rectangular, generally trapezoidal, or generally oval. The first end of the post 104 is engaged to the posterior end of the marking head 108 and extends distally from the posterior end of the marking head 108.

The marking end of the marking head 108 comprises at least one marking tip (109A, 109B). As illustrated in the exemplary embodiment in FIGS. 2 and 3, two marking tips (109A, 109B) are positioned on the marking head 108. However, it should be noted that the marking head 108 may contain a plurality of marking tips. The term marking tips refers to a tip that can place a mark or an indicator on the surface of the cornea, sclera, or the sclera/cornea junction (also collectively referred to as the surface of the eye). The marking tip may be pre-inked, whereby the tip is infused with ink prior to shipment to the user and the user does not constantly have to apply ink to the tip. Additionally, the tip may be used repetitively, if necessary, on the same patient for providing more than one mark without having to constantly apply ink. Alternatively, the tip may apply a tack or other like indicator on the surface of the cornea, sclera, or the sclera/cornea junction.

As illustrated in FIG. 3, a pair of slots (110A, 110B) are disposed on the marking end of the marking head 108 for receiving the marking tips (109A, 109B). The slots (110A, 110B) are positioned at a predetermined location on the marking head 108 for the receipt of the marking tips (109A, 109B) for providing a mark or indication. In another alternative embodiment, the marking head 108 contains marking tips that are integral with the marking head 108 and the marking tips are not inserted into slots. In another version, the entire marking means 101 could be made of porous marking material.

The post 104 has a first end and a second end, whereby the post 104 extends distally from the posterior end of the marking means 101. Preferably, the post 104 is hollow, has a hollow interior portion, or is made of a clear material to allow light to pass through the interior portion of the post 104. An annular ring 111 is disposed around the exterior of the post 104 and is positioned in close proximity to the second end of the post 104. The annular ring 111 contains a position indicator 112 disposed on the external surface of the annular ring 111. The position indicator 112 may be placed on the interior surface of the annular ring 111 as a groove that is pigmented. The position indicator 112 as illustrated in FIG. 3 consists of a marking or arrow for providing a visual representation. At least one radially protruding support means, such as a rib, 113 is positioned on the annular ring 111 and extends along the post 104 towards the first end of the post and the marking head 108. As illustrated in FIG. 3, a series of spaced-apart radially protruding ribs 113 are disposed on the annular ring and positioned an equal distance apart. The radially protruding ribs 113 extend along the post 104 towards the first end of the post and the marking head 108. The ribs 113 serve as a support for the marking means 101.

As mentioned above, the marking disk 108 may be a single marker head, thus eliminating the need for marking tips. In other words, the marking disk 108 is engaged to the post 104 and provides a mark or indicator on the cornea, sclera, or cornea/sclera junction. In one embodiment, the marking disk 108 is infused with ink and leaves a mark on the exterior surface of the eye.

As illustrated in FIG. 2, the marking means 101 is housed within the sleeve 102. The sleeve 102 has a closed end 106 and an open end 107. The purpose of the sleeve 102 is to protect the marking tips (109A, 109B) from exposure during shipment and assembly. In an alternative embodiment, the sleeve 102 may contain an ink pad or the like, allowing the marking tips (109A, 109B) to be infused with ink each time the marking means 101 is placed within the sleeve 102.

Figures 4A, 4B:
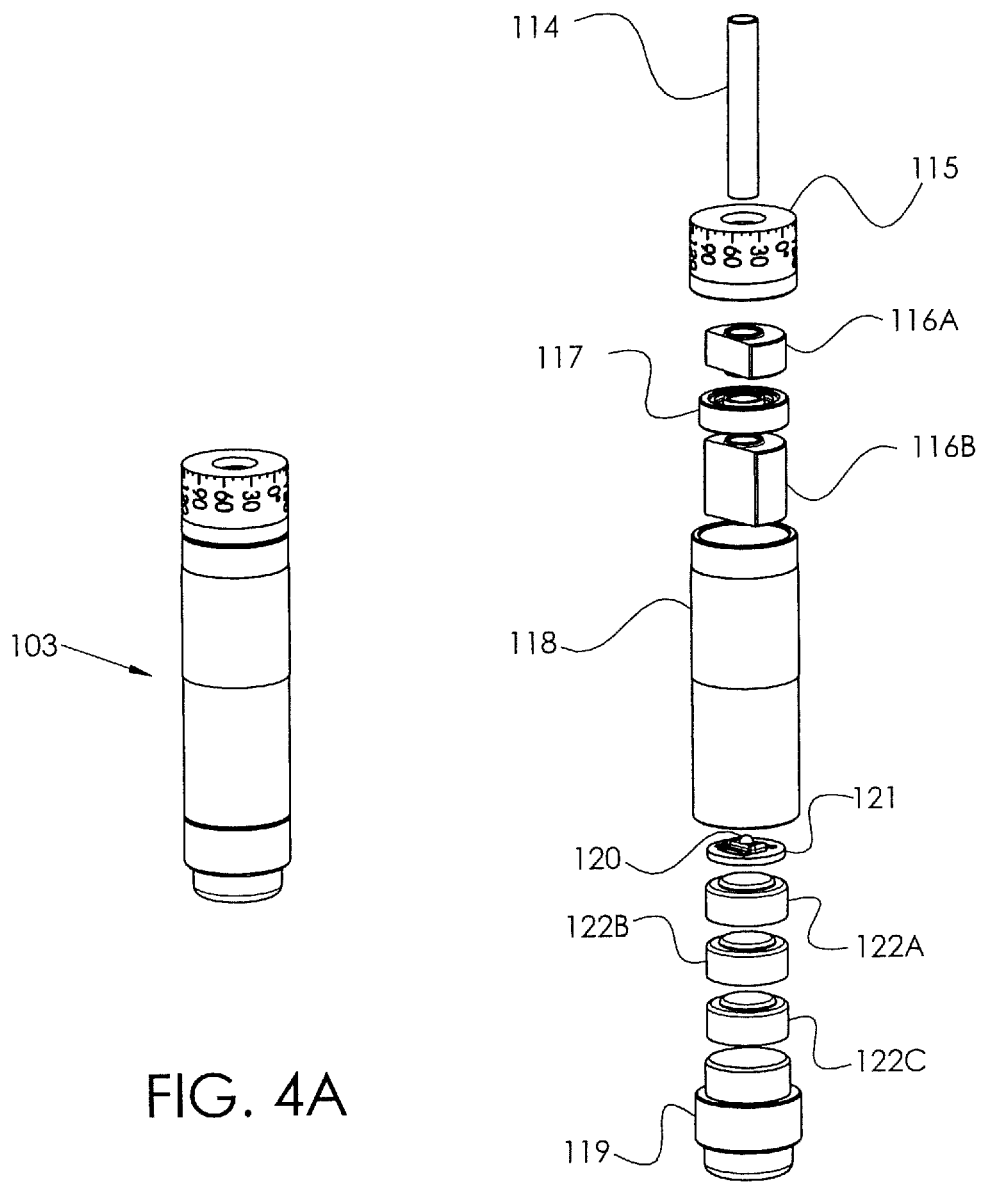
FIG. 4A is a perspective view of the handle.
FIG. 4B is an exploded view of the handle.

The handle 103 is generally cylindrical and contains a hollow cavity for receiving the internal components of the eye marker device 100 and has an outer surface and an inner surface. The handle 103, as illustrated in FIGS. 4A and 4B, receives one or more of the following: a hollow mounting shaft 114, a rotational scale 115, at least one weight (116A, 116B), and a bearing 117. The exterior surface of the bearing 117 is engaged to the interior surface of the handle 103 with the bore of the bearing centrally positioned within the hollow cavity. The hollow mounting shaft 114 is received within the bore of the bearing 117 and positioned within the hollow cavity on the handle 103 towards the proximal end. The hollow mounting shaft 114 contains a first end and a second end. The first end of the hollow mounting shaft 114 is press fitted into a centrally located bore of the rotational scale 115, allowing the rotational scale 115 to extend proximally from the exterior handle wall 118. The hollow mounting shaft 114 can be composed of a clear plastic or plastic composition so that it is transparent. The hollow mounting shaft 114 may also be hazy or opaque and composed of any suitable material other than plastic. The at least one weight (116A, 116B) is rotationally engaged to the hollow mounting shaft 114. The at least one weight (116A, 116B) contains a centrally located bore for receiving the hollow mounting shaft 114. The shaft 114, rotational scale 115, and at least one weight (116A, 116B) may have detents to properly align the rotational scale 115 with the weight 116.

Figure 6A:
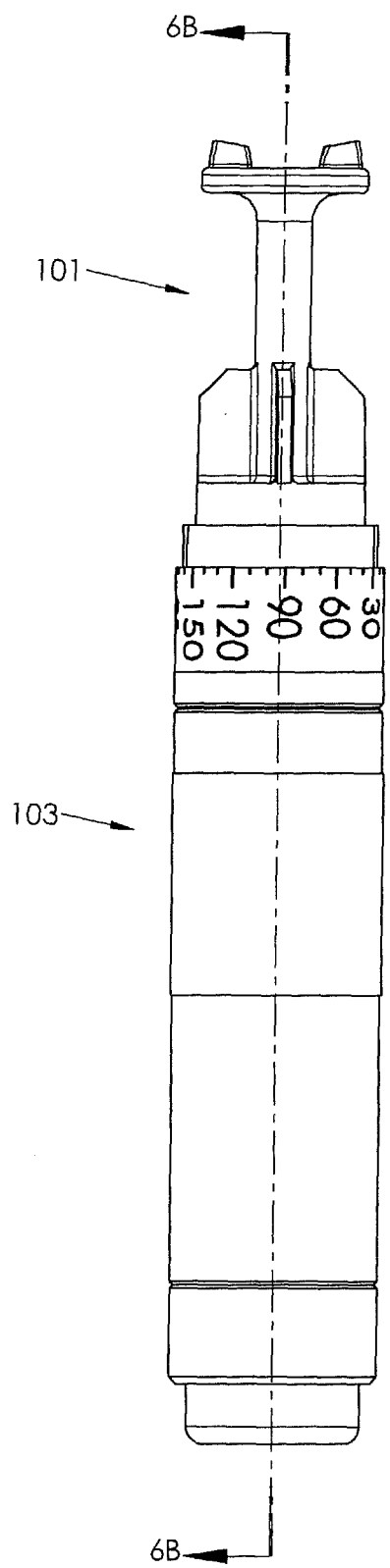
FIG. 6A is a perspective view of the eye marker device with a handle.
Figure 6B:
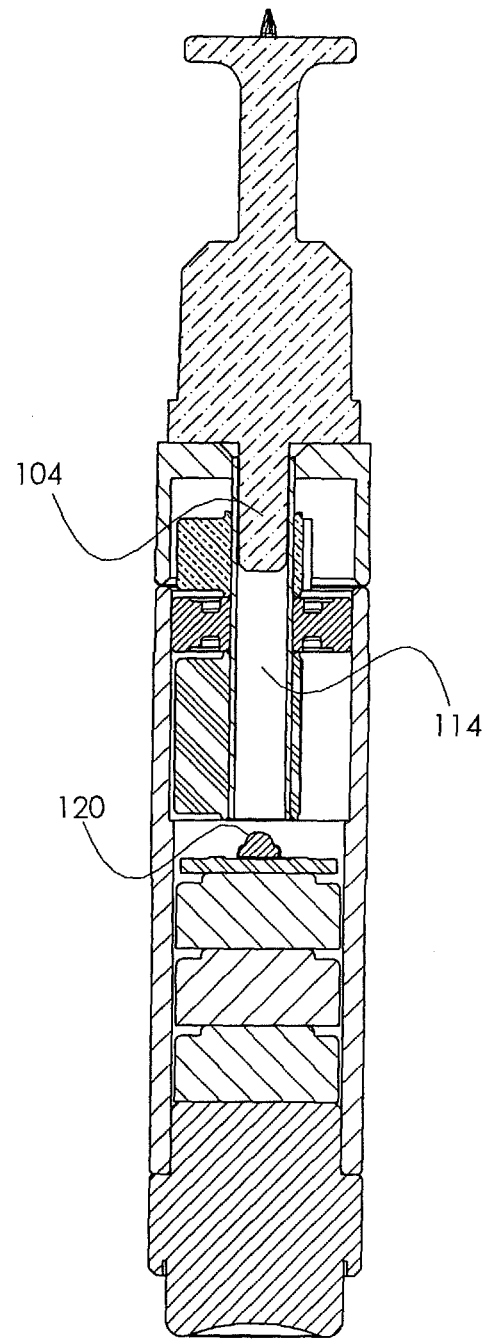
FIG. 6B is a cut-away view along the line 6B of FIG. 6A.
Figure 7:
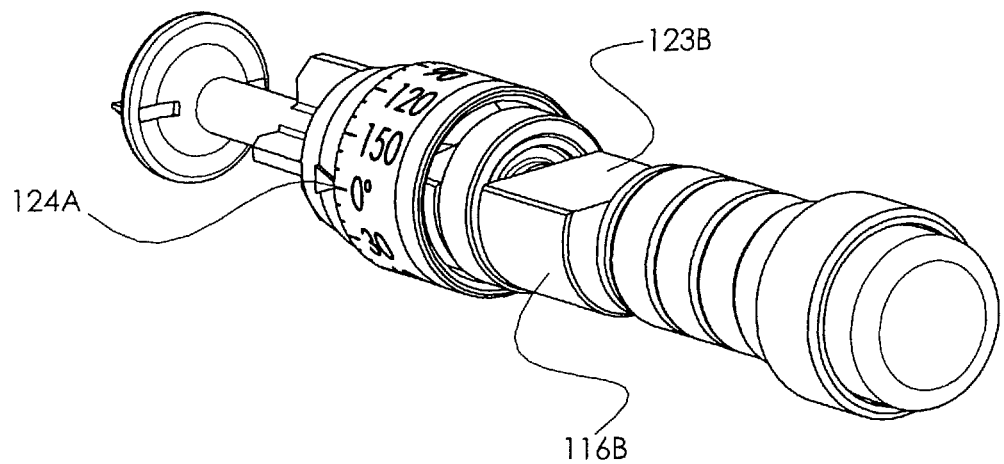
FIG. 7 is a perspective view of the eye marker device with a disposable tip without an external handle shell.

As illustrated in FIGS. 4B, 6B, and 7, the eye marker device 100 may contain two weights (116A, 116B) that are rotationally engaged in a spaced-apart relationship on the hollow mounting shaft 114. The weights (116A, 116B) are not engaged to one another and are allowed to rotate independently from one another for providing internal balancing, stability, and/or rotational alignment of the eye marker device 100. The weights (116A, 116B) and bearing 117 are enclosed, but free to rotate, within the handle 103.

An activation mechanism 119 is located at the most distal end of the handle 103. The activation mechanism 119 may be rotated, clicked, or otherwise manipulated to activate and deactivate a light source 120 disposed on an enclosed electrical circuit 121. In other words, the activation mechanism 119 is a switch for operating the light source 120. In a preferred embodiment, the light source is an LED, which may change colors to keep the user's eyes fixated on the light emanating from the LED or light source. The enclosed electrical circuit 121 is known to one of ordinary skill in the art to provide electricity from the power source to the light source 120. The electrical circuit may also include a timer that prevents the flow of electricity to the light source 120 and turns the light source 120 "off." The timer can have a predetermined time limit to prevent the flow of electricity. For instance, the timer may allow the flow of electricity, wherein the light source 120 is "on", and after five minutes, the flow of electricity ceases to the light source 120 and the light is turned "off." Additionally, a timer or like mechanism may be included within the electrical circuit allowing the light to blink or turn "on" and "off" periodically. The fixation light source is designed to mimic the fixation light commonly used in ophthalmic diagnostic equipment in a manner that would be known to one of ordinary skill in the art.

As mentioned above, the eye marker device 100 is equipped with at least one power source. As illustrated in FIG. 4B, the power source is a series of power cartridges 122A, 122B, and 122C disposed between the circuit and the activation mechanism. The power cartridges 122A, 122B, and 122C are batteries arranged in series and may be single use batteries or rechargeable batteries. Additionally, any number of batteries may be utilized, including one battery, two batteries, or a plurality of batteries. The eye marker device 100 may be engaged to a recharging base for recharging the power cartridges 122A, 122B, and 122C. Alternatively, the power source may be an electrical connector that receives power from an external source, such as an electrical wall outlet.

It should be noted that the marking means 101 may be disposable and the handle 103 may be disposable. However, the marking means 101 and handle 103 may be reusable. Alternatively, the marking means 101 may be disposable but the handle 103 is reusable, or vice versa, the marking means 101 is reusable and the handle 103 is disposable. In yet another alternative embodiment, the marking means 101 and handle 103 are pre-assembled as a single integral unit, designed for a single-use and then disposed of.

Figure 5:
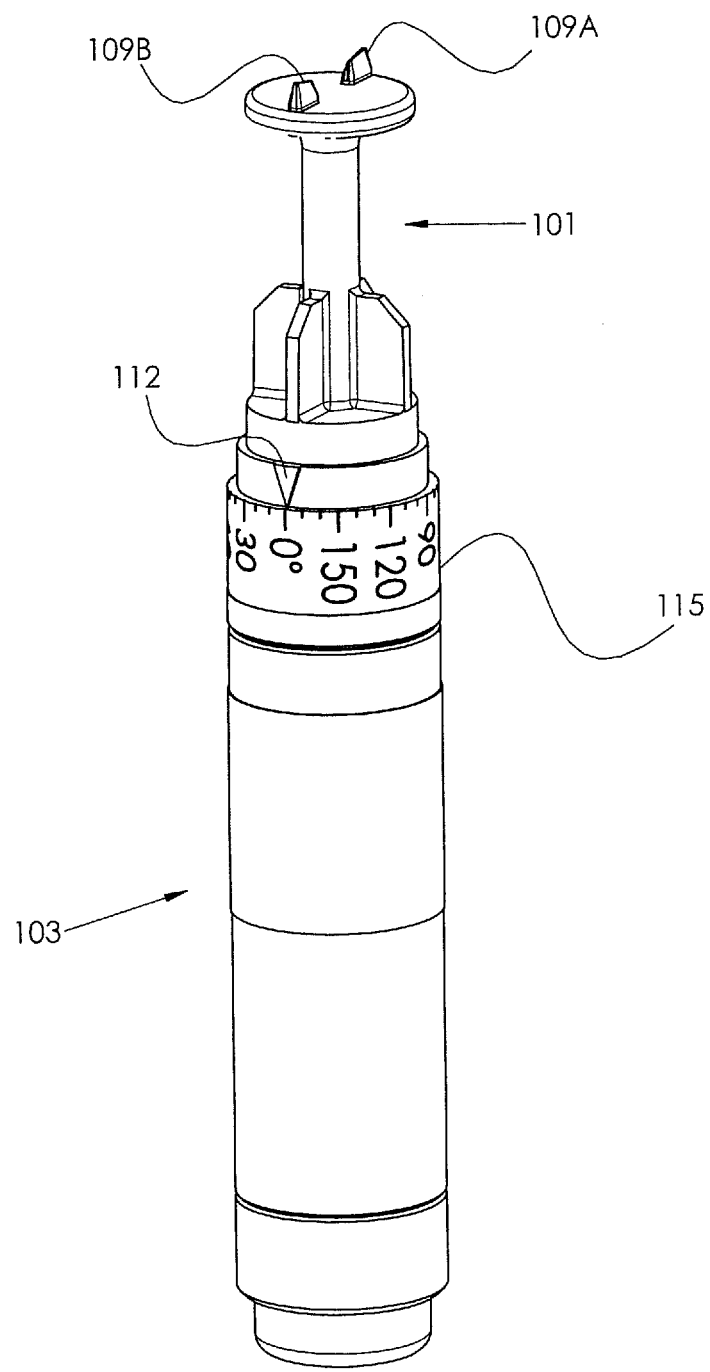
FIG. 5 is a perspective view of the eye marking device.

A partially assembled device 100 is illustrated in FIG. 5. The marking means 101 is positioned on the handle 103. The marking means 101 is engaged to the handle 103 by way of friction fit into the central cavity of the hollow mounting shaft 114. The post 104 of marking means 101 is received within a centrally located bore of the rotational scale 115 and proceeds through the centrally located bore and is received within the central cavity of the hollow mounting shaft 114. The post 104 may be releasably engaged to the hollow mounting shaft 114 for a disposable marking means 101 or may be integral or permanently affixed to the hollow mounting shaft 114. The post 104 rotates within the centrally located bore of the rotational scale 115, and annular ring 111 and position indicator 112 rotates with respect to the rotational scale 115. The position indicator 112 provides a visual representation of the angle of the marking means 101 relative to a predetermined origination point.

As shown in FIG. 5, the sleeve 102 has been removed and the position indicator 112 on the marking means 101 may be positioned according to the rotational scale 115 for providing accurate placement of marking tips 109A, 109B on the target area. The post 104 located on the distal end of the marking means 101 is inserted into the hollow mounting shaft 114 in the handle 103, as shown in FIGS. 6A and 6B. The hollow mounting shaft 114 and post 104 are positioned so that light from the LED 120 is projected through the center of both the post 104 and hollow mounting shaft 114 for projecting light through the means 101.

As illustrated in FIG. 7, the weights 116A (not shown) and 116B consist of a generally cylindrical shape with a flat portion (123B, 123A not shown) on one side. During the assembly of the device 100, the flat side of the weights 116A, 116B is aligned with the 0° indicators (124A, 124B not shown) on the rotational scale 115. The rotational imbalance of the weights 116A, 116B allows the user to shake the device, thus imparting force to the weights 116A, 116B, to align the rotational scale 115 with the horizon when the weights come to rest. The shaft 114, rotational scale 115, and at least one weight (116A, 116B) may have detents to properly align the rotational scale 115 with the at least one weight 116.

In another alternative embodiment of the present invention, the device 100 may be equipped with other attachment means in place of the post 104 and open end 105 for securing the marking means 101 to the handle 103. By way of example only, the attachment means may consist of the following, but not limited to, threads, a bayonet-type fitting, and the like. Likewise, the alternative attachment means could be used to attach the disposable maker to a disposable handle.

In another alternative embodiment, the weights 116A, 116B and bearing 117 may also be designed such that the alignment means is provided by a swinging pendulum or the like. Additionally, the imbalanced weights 116A, 116B may include a plurality of shapes, the only requirement being that the weights 116A, 116B remain unbalanced such that, after agitation, the weights try to find a vertical or horizontal equilibrium.

In another alternative embodiment, the handle 103 may be designed without an internal illuminating source, such as the LED 120 and activation mechanism.

In another alternative embodiment, the device 100 may also be alternatively equipped with other marking means, including, but not limited to, one or more marking tips or pads consisting of a plurality of shapes. Additionally, the marking disk 108 may consist of a plurality of shapes including, but not limited to, circles, shapes with one or more vertices or shapes having concave or convex geometries.

In manufacturing the device 100, adhesives may be employed to substantially join the components in the described embodiment, particularly the marking tips 109A, 109B, rotational scale 115, and imbalanced weights 116A, 116B. Adhesives may include, but are not limited to, cyanoacrylate, 2-part epoxy, heat-activated resin, UV cured adhesive and hot melt. Joining may also be achieved through, but not limited to, the use of solvent bonding, ultrasonics, and heat-staking means.

The marking means 101 may be made of molded porous plastic that contains marking tips (109A, 109B) in a plurality of configurations. A single marking tip may be attached to the marking head 108 or a single marking tip may be attached to the first end of the post 104 by various means and configurations, thus eliminating the need for the marking head 108. In another alternative embodiment, the marking means 101 may be composed of porous plastic containing a post 104 with a hollow cavity to allow the passage of light from the light source 120, through the handle 103, and to the marking head 108.

The marking tips (109A, 109B) may be of any shape or configuration for placing a mark or indicator on the surface of the eye. The marking tips (109A, 109B) may be composed of bonded fiber, porous plastic, a porous material such as paper, cork, expanded styrofoam, aerogels, or any like material that may be infused to hold or contain an indicator, pigment, or ink. The marking tips (109A, 109B) may also contain any material containing a formed indicator reservoir or a channel with passive flow to the surface. The marking tips (109A, 109B) may be of any material with nanotubules/channels or the like or with a material containing pigment/indicator encapsulated microbeads/granules that are able to release the indicator upon contact with pressure, water, the tear film, heat, or other release mechanism. Further, the marking tips (109A, 109B) may contain a microprint cartridge like mechanism where the indicator is jetted from the marking tips (109A, 109B) in a favorable pattern by an electronic or non-electronic mechanism. The marking tips (109A, 109B) may contain or be attached to a compressible reservoir of indicator/ink such that compression forces the indicator/ink to the surface of the marking tip (109A, 109B). The marking tips (109A, 109B) may be coated with a bicompatible glue or gel that is itself covered with the indicator/ink such that the glue or gel acts as an adhesive to keep the indicator/ink attached to the marking tips (109A, 109B) and such that the indicator/ink constitutes the external surface of the marking tip/glue/gel complex, or the marking tips (109A, 109B) may be a biocompatible glue or gel that is mixed with the indicator such that the composite of the glue/gel/indicator/ink constitutes the external surface of the nib.

In another alternative embodiment, the marking means 101, marking tips (109A, 109B), or handle 103 may contain a biasing element or a damping element for absorbing force when the device 100 is in use. The biasing element, such as a spring, or damping element would compress slightly when the device 100 is in contact with the exterior of the eye. The compression or damping effect caused by the biasing element or damping element allows the patient to be more comfortable during the procedure and allows a "soft touch" to the exterior of the eye. The biasing and damping element may be engaged to the device in a multitude of ways. For example, the biasing and damping element would be engaged between the first end of the post 104 and the posterior end of the marking head 108. Alternatively, the biasing element or damping element may be engaged to the hollow mounting shaft 114 for operational engagement with the marking means 101. In another alternative embodiment, the biasing element or damping element may be positioned adjacent the marking tips (109A, 109B).

The purpose of the device 100 is to provide preoperative eye marks that can be placed at the desired axis of astigmatic correction with a high level of accuracy, and that can be placed well in advance of the surgery allowing optimal patient flow. The active marking member is disposable, so no sterilization is needed as with the reusable metal markers. The one use aspect avoids any sterilization issues and improves patient flow since there is no wait for sterilization to be accomplished. The marking tip and sleeve are designed to provide an inexpensive, sterile attachment that can be disposed of after use. The remainder of the device may or may not be sterilized between use. The disposable tip includes a cylindrical post that is oriented during assembly to be in-line with the illuminating component of the device. This illumination travels through the cylindrical post to provide a focal point for the patient during marking of the eye. The imbalanced weights are assembled such that the weights seek a vertical and horizontal equilibrium with which the rotating scale on the device is aligned. After equilibrium is reached, the rotating scale provides a point of reference for the marking tip with which the tip can apply markings at any number of desired angles.

Figure 8:
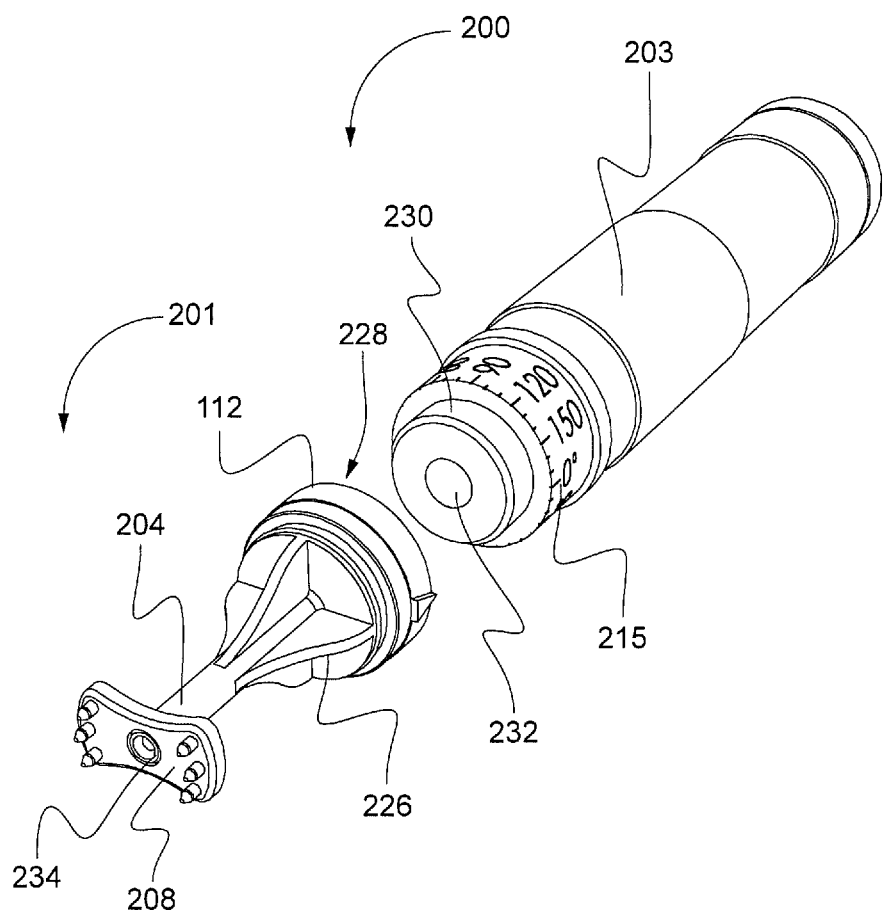
FIG. 8 is a perspective view of an alternative embodiment of the eye marker device.
Figure 9:
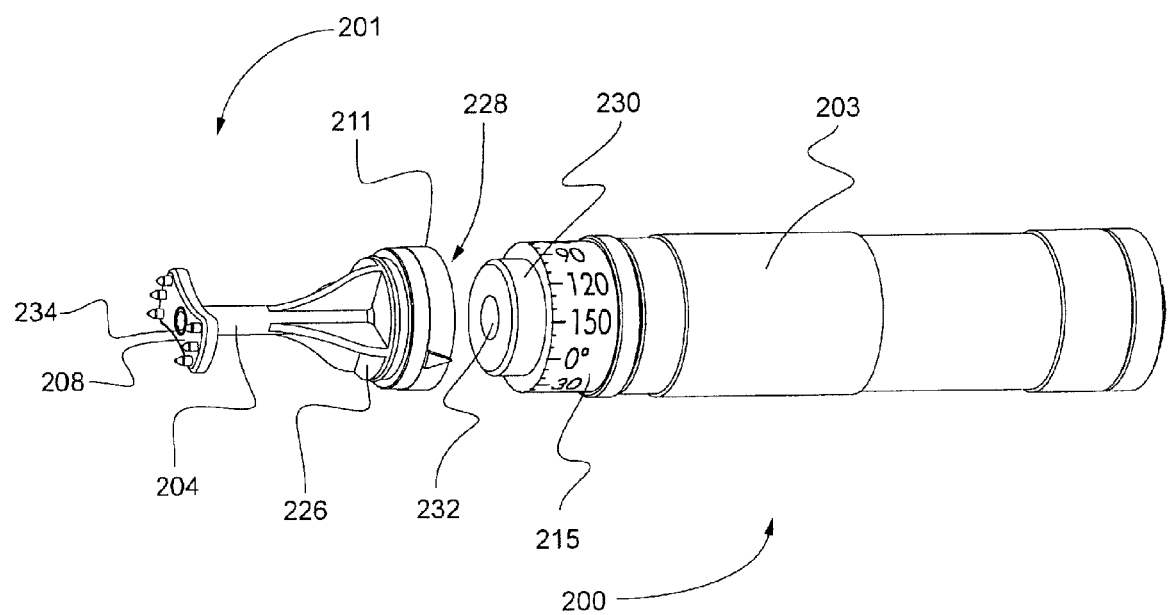
FIG. 9 is a perspective side view of an alternative embodiment of the eye marker device.

Another alternative embodiment is illustrated in FIGS. 8 and 9. The eye marker device 200 includes a marking means 201 and a handle 203. The marking means 201 contains a post 204 with a first end and a second end, whereby the post 204 extends distally from the first end of the marking means 201. A marking head 208 is disposed on the first end of the marking means 201 and contains a marking end and a posterior end. The marking head 208 is generally rectangular shaped with a converging center portion, but may be alternatively shaped, by way of example only, and not limited to, generally square, generally rectangular, generally circular, generally trapezoidal or generally oval.

The marking end of the marking head 208 comprises at least one marking tip. As illustrated in the exemplary embodiment in FIGS. 8 and 9, a plurality of marking tips are positioned on the marking head 208. However, it should be noted that the marking head 208 may contain any number of marking tips, including a single marking tip. The term marking tips refers to a tip that can place a mark or an indicator on the surface of the cornea, sclera, or the sclera/cornea junction (also collectively referred to as the surface of the eye). The marking tip may be pre-inked, whereby the tip is infused with ink prior to shipment to the user and the user does not constantly have to apply ink to the tip. Alternatively, the tip may apply a tack or other like indicator on the surface of the cornea, sclera, or the sclera/cornea junction.

Figure 10:
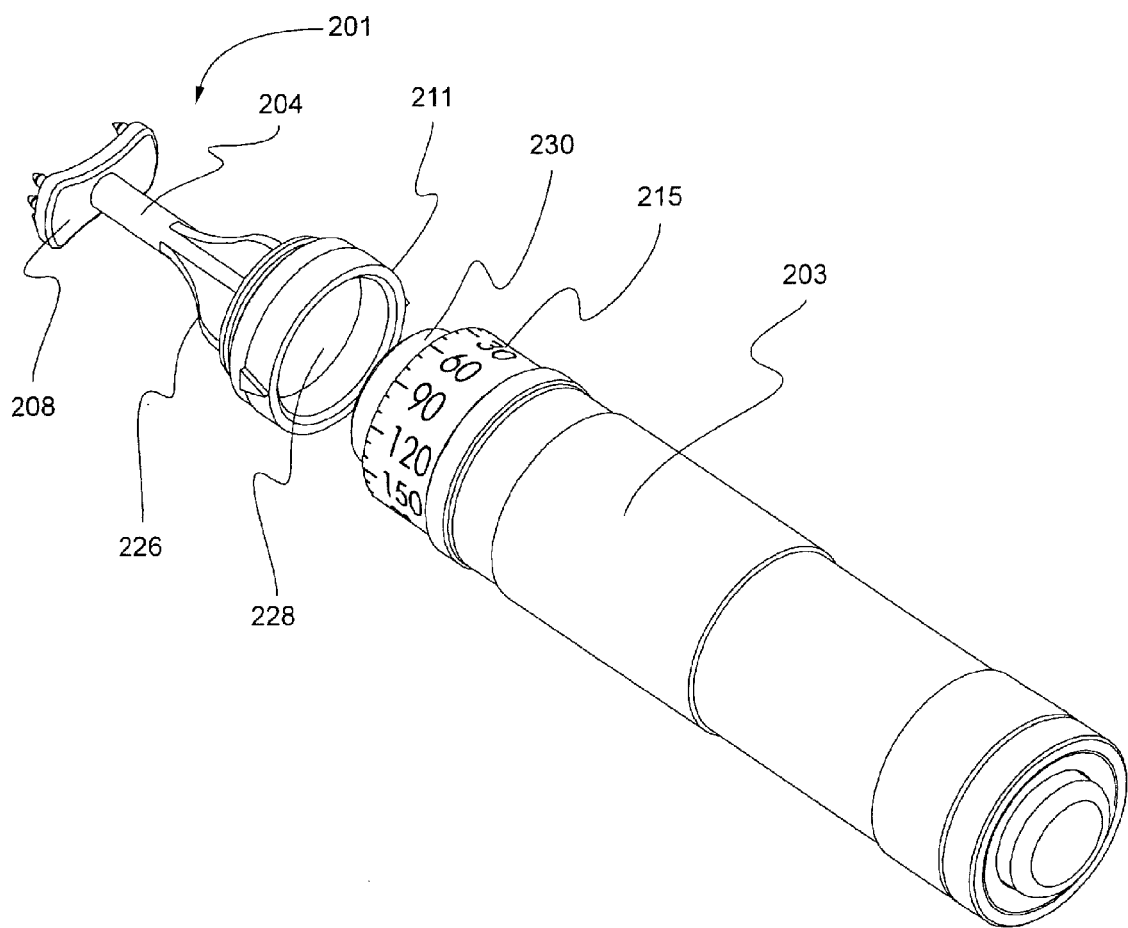
FIG. 10 is a perspective view of an alternative embodiment of the eye marker device.
Figure 11:
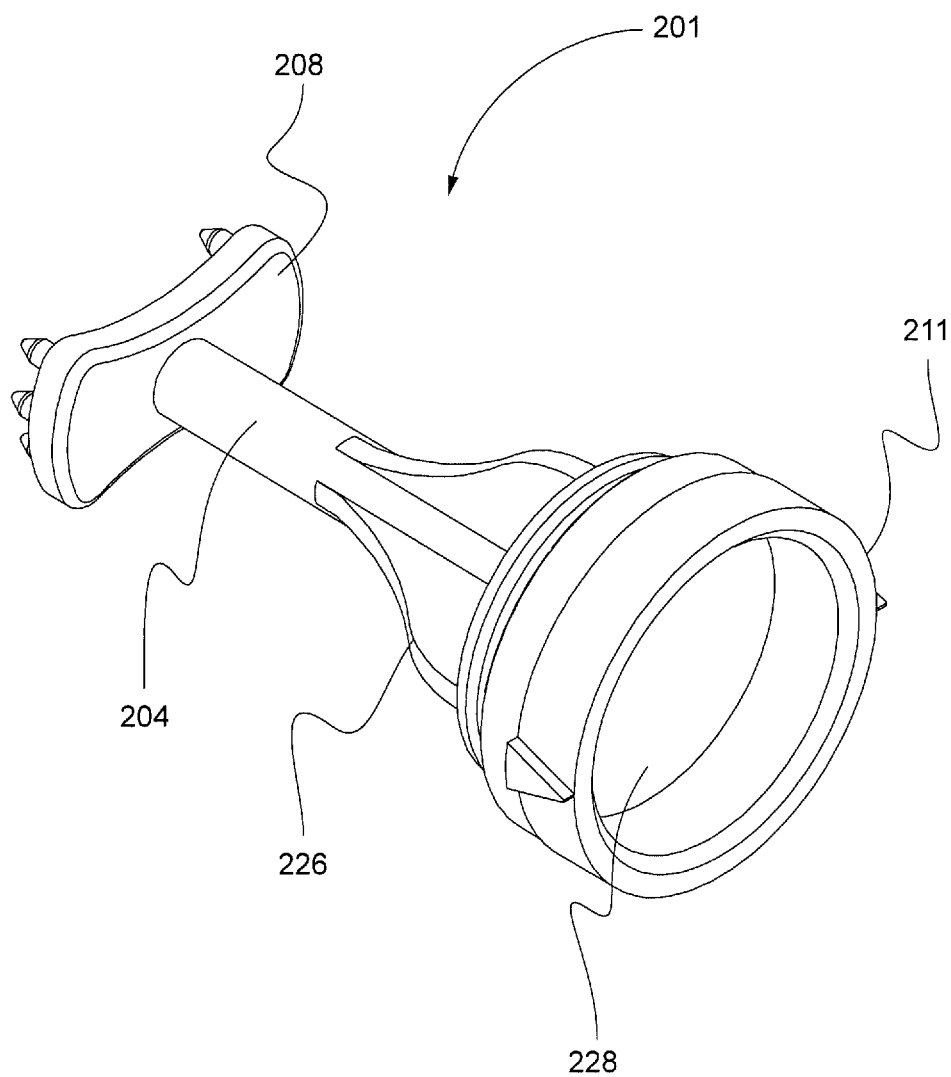
FIG. 11 is a perspective view of an alternative embodiment of the marking means of the alternative embodiment of the eye marker device of FIG. 10.
Figure 12:
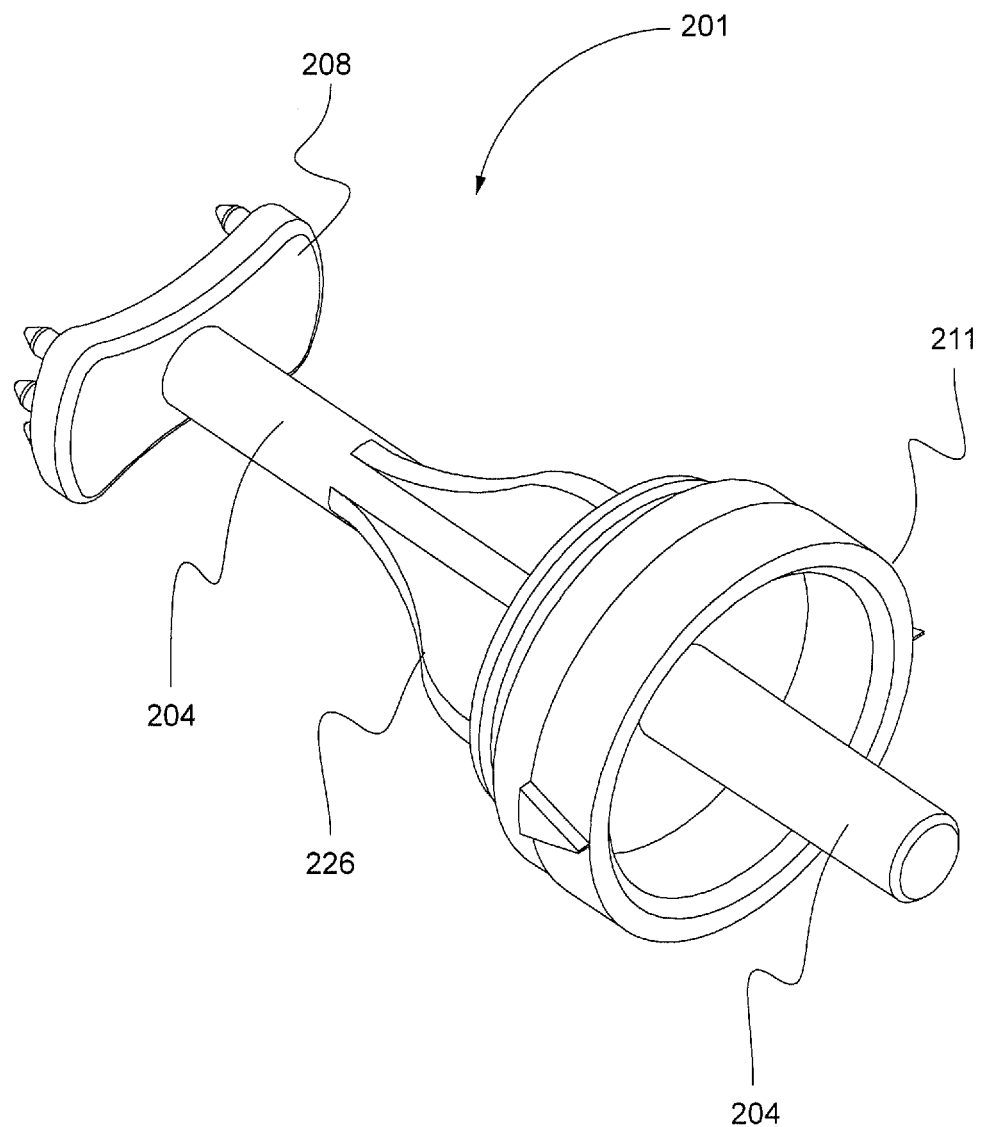
FIG. 12 is a perspective view of another alternative embodiment of the marking means of the alternative embodiment of the eye marker device of FIG. 10.

As illustrated in FIGS. 10 and 11, a base 226 is engaged to the second end of the post 204 and contains an outer circumference. An annular ring 211 is disposed on the outer surface and extends away from the marking means 201 forming a cavity 228 therein. Alternatively, the post 204 may extend through the base 226 and protrude into the cavity 228, as shown in FIG. 12.

The handle 203 contains a hub 230 on the posterior end. The hub 230 is generally circular in shape and has a diameter less than the diameter of the handle 203. The central bore of the rotational scale 215 is received within the hub 230 forming a rotational engagement and the exterior side of the rotational scale 215 forms a shelf for receiving the outer edge of the annular ring 211. The hub 230 is received within the cavity 228 of the marking means 201 forming a selectively secured arrangement. The upper portion of the hub 230 contains a chamfered portion to guide the hub 230 into the cavity 228. The outer edge of the annular ring 211 rests upon the shelf formed by the exterior side of the rotational scale 215.

In another embodiment, the hub 230 may contain a receiving portion 232 as shown in FIG. 9, that is generally a cylindrical bore. In the embodiment including a post 204 that may extend within the cavity 228, the post 204 is received within the receiving portion 232 forming a selectively secured arrangement. In this embodiment, the post 204 is received within the receiving portion 232 and the hub 230 is received within the cavity 228 forming a selectively secured embodiment. The outer edge of the annular ring 211 rests upon the shelf formed by an exterior side of the rotational scale 215.

An alternative embodiment of the marking means 201 is also illustrated in FIGS. 8 and 9. The marking means 201, as illustrated, may contain a fixation device 234 that is centrally disposed on the marking head 208. Generally, the fixation device 234 is positioned adjacent the hollow cavity of the post 204. The fixation device 234 may include a fixation lens, fixation imprint, or a fixation target.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:
1. An eye marker device, comprising:
a handle having an interior cavity;
a mounting shaft disposed within the handle;
a marking device engaged to the mounting shaft;
at least one marking tip disposed on the marking device;
a rotational scale for providing a visual representation of an angle of the marking device; and
at least one weight rotationally engaged to the hollow mounting shaft and freely rotatable with respect to the handle.

2. The eye marker device of claim 1, wherein the marking device further comprises a marking head with a marking end and a posterior end that contains at least one marking tip disposed on the marking end.

3. The eye marker device of claim 1, further comprising a marking head with at least two marking tips.

4. The eye marker device of claim 1, further comprising two weights disposed within the handle for providing balance, stability or rotational alignment to the eye marker device.

5. The eye marker device of claim 1, further comprising a bearing positioned within the interior cavity of the handle having a centrally located bore for receiving the mounting shaft, wherein the at least one weight is rotationally engaged to the hollow mounting shaft for providing balance, stability or rotational alignment to the eye marker device.

6. An eye marker device, comprising:
a handle having an interior cavity;
a mounting shaft disposed within the handle;
a marking device engaged to the mounting shaft;
a light source allowing light to shine through the interior cavity of the handle;
a rotational scale for providing a visual representation of an angle of the marking device; and
at least one weight rotationally engaged to the hollow mounting shaft and freely rotatable with respect to the handle.

7. The eye marker device of claim 6, wherein the marking device is disposable.

8. The eye marker device of claim 6, wherein the marking device comprises:
a post having a first end and a second end;
a marking head engaged to the first end of the post and having a marking end and a posterior end, whereby the first end of the post is engaged to the posterior end of the marking head; and at least one marking tip engaged to the marking end of the marking head.

9. The eye marker device of claim 6, wherein the light source is an LED disposed on an enclosed electrical circuit.

10. The eye marker device of claim 6, further comprising a sleeve for enclosing the marking device.

\* \* \* \* \*